(12) United States Patent
de Moura

(10) Patent No.: US 8,540,752 B2
(45) Date of Patent: Sep. 24, 2013

(54) INTERSPINOUS MESH

(75) Inventor: Alexandre de Moura, Garden City, NY (US)

(73) Assignee: Spine Tek, Inc., Westbury, NY (US)

( * ) Notice: Subject to any disclaimer, the term of this patent is extended or adjusted under 35 U.S.C. 154(b) by 109 days.

(21) Appl. No.: 12/667,310

(22) PCT Filed: Jun. 27, 2008

(86) PCT No.: PCT/US2008/068486
§ 371 (c)(1),
(2), (4) Date: Nov. 3, 2010

(65) Prior Publication Data
US 2011/0054532 A1    Mar. 3, 2011

Related U.S. Application Data

(60) Provisional application No. 60/958,149, filed on Jul. 3, 2007.

(51) Int. Cl.
*A61B 17/70*   (2006.01)

(52) U.S. Cl.
USPC .......................................................... 606/249

(58) Field of Classification Search
USPC .................................................. 606/248, 249
See application file for complete search history.

(56) References Cited

U.S. PATENT DOCUMENTS

| | | | |
|---|---|---|---|
| 3,550,304 A | 12/1970 | Kuslich | |
| 4,364,392 A * | 12/1982 | Strother et al. | 606/195 |
| 4,441,495 A * | 4/1984 | Hicswa | 606/195 |
| 4,517,979 A * | 5/1985 | Pecenka | 606/195 |
| 4,545,367 A * | 10/1985 | Tucci | 128/898 |
| 4,932,969 A | 6/1990 | Frey et al. | |
| 5,015,255 A | 5/1991 | Kuslich | |
| 5,059,193 A | 10/1991 | Kuslich | |
| 5,062,845 A | 11/1991 | Kuslich et al. | |
| 5,445,639 A | 8/1995 | Kuslich et al. | |
| 5,458,638 A | 10/1995 | Kuslich et al. | |
| 5,489,307 A | 2/1996 | Kuslich et al. | |
| 5,489,308 A | 2/1996 | Kuslich et al. | |
| 5,549,679 A | 8/1996 | Kuslich | |
| 5,571,189 A | 11/1996 | Kuslich | |
| 5,591,235 A | 1/1997 | Kuslich | |
| 5,700,291 A | 12/1997 | Kuslich et al. | |
| 5,720,748 A | 2/1998 | Kuslich et al. | |
| 5,895,427 A | 4/1999 | Kuslich et al. | |
| 5,899,908 A | 5/1999 | Kuslich et al. | |
| 5,928,242 A | 7/1999 | Kuslich et al. | |

(Continued)

FOREIGN PATENT DOCUMENTS

| WO | 2005009300 A1 | 2/2005 |
|---|---|---|
| WO | 2007110604 A1 | 10/2007 |

OTHER PUBLICATIONS

ISA/US.; Written Opinion; Sep. 9, 2008; 5 pages.

*Primary Examiner* — Ellen C Hammond
(74) *Attorney, Agent, or Firm* — Keusey & Associates, P.C.

(57) ABSTRACT

In accordance with one or more implementations of the present invention, a flexible mesh bag including a catenoidal central portion (106) and two bulbous end portions (104, 108) may be employed as a spinal spacer. The mesh may be percutaneously implanted between adjacent spinous processes (202, 204) to correct the position and orientation of a spine and thereby relieve any discomfort associated with spinal stenosis. Additionally, the mesh may be filled with a bone graft material to permit bone fusion for long-term stability.

8 Claims, 4 Drawing Sheets

(56) References Cited

U.S. PATENT DOCUMENTS

| | | |
|---|---|---|
| 5,947,971 A | 9/1999 | Kuslich et al. |
| 5,989,256 A | 11/1999 | Kuslich et al. |
| 6,056,749 A | 5/2000 | Kuslich |
| 6,086,589 A | 7/2000 | Kuslich et al. |
| 6,149,686 A | 11/2000 | Kuslich et al. |
| 6,199,551 B1 | 3/2001 | Kuslich |
| 6,287,343 B1 | 9/2001 | Kuslich et al. |
| RE37,479 E | 12/2001 | Kuslich |
| 6,383,188 B2 | 5/2002 | Kuslich et al. |
| 6,391,058 B1 | 5/2002 | Kuslich et al. |
| 6,434,799 B1 | 8/2002 | Kuslich et al. |
| 6,599,320 B1 | 7/2003 | Kuslich et al. |
| 6,620,162 B2 | 9/2003 | Kuslich et al. |
| 6,620,169 B1 | 9/2003 | Peterson et al. |
| 6,706,044 B2 | 3/2004 | Kuslich et al. |
| 6,712,853 B2 | 3/2004 | Kuslich |
| 6,959,470 B2 | 11/2005 | Kuslich et al. |
| 7,025,771 B2 | 4/2006 | Kuslich et al. |
| 7,056,345 B2 | 6/2006 | Kuslich |
| 7,135,026 B2 | 11/2006 | Kuslich et al. |
| 7,220,282 B2 | 5/2007 | Kuslich |
| 7,226,481 B2 | 6/2007 | Kuslich |
| 7,722,621 B2 | 5/2010 | Kuslich et al. |
| 7,985,246 B2 * | 7/2011 | Trieu .............................. 606/279 |
| 2001/0025401 A1 | 10/2001 | Kuslich et al. |
| 2001/0029645 A1 | 10/2001 | Kuslich et al. |
| 2001/0034526 A1 | 10/2001 | Kuslich et al. |
| 2002/0010472 A1 | 1/2002 | Kuslich et al. |
| 2002/0068974 A1 | 6/2002 | Kuslich et al. |
| 2002/0077701 A1 | 6/2002 | Kuslich |
| 2002/0115949 A1 | 8/2002 | Kuslich et al. |
| 2002/0169449 A1 | 11/2002 | Kuslich et al. |
| 2002/0183846 A1 | 12/2002 | Kuslich et al. |
| 2003/0018292 A1 | 1/2003 | Kuslich et al. |
| 2003/0019082 A1 | 1/2003 | Kuslich et al. |
| 2003/0083746 A1 | 5/2003 | Kuslich |
| 2003/0083749 A1 | 5/2003 | Kuslich et al. |
| 2003/0181982 A1 | 9/2003 | Kuslich |
| 2004/0006348 A1 | 1/2004 | Peterson et al. |
| 2004/0073308 A1 | 4/2004 | Kuslich et al. |
| 2004/0082957 A1 | 4/2004 | Stephen et al. |
| 2004/0267368 A1 | 12/2004 | Kuslich |
| 2005/0043752 A1 | 2/2005 | Phan et al. |
| 2005/0055094 A1 | 3/2005 | Kuslich |
| 2005/0131417 A1 | 6/2005 | Ahern et al. |
| 2006/0149379 A1 | 7/2006 | Kuslich et al. |
| 2006/0264960 A1 | 11/2006 | Kuslich et al. |
| 2007/0016214 A1 | 1/2007 | Kuslich et al. |
| 2007/0016300 A1 | 1/2007 | Kuslich |
| 2007/0233076 A1 * | 10/2007 | Trieu ............................... 606/61 |
| 2007/0270823 A1 * | 11/2007 | Trieu et al. ...................... 606/61 |
| 2007/0276497 A1 * | 11/2007 | Anderson .................. 623/17.12 |
| 2008/0045952 A1 | 2/2008 | Kuslich |
| 2008/0086115 A1 * | 4/2008 | Stoklund et al. .................... 606/1 |
| 2008/0086133 A1 | 4/2008 | Kuslich et al. |
| 2009/0118833 A1 * | 5/2009 | Hudgins et al. ............ 623/17.16 |
| 2009/0125110 A1 | 5/2009 | Kuslich |
| 2009/0326581 A1 * | 12/2009 | Galley et al. ................... 606/249 |
| 2010/0049251 A1 | 2/2010 | Kuslich et al. |
| 2010/0113290 A1 | 5/2010 | Klass et al. |
| 2010/0152855 A1 | 6/2010 | Kuslich |
| 2010/0184046 A1 | 7/2010 | Klass et al. |
| 2010/0203529 A1 | 8/2010 | Kuslich et al. |
| 2010/0256648 A1 | 10/2010 | Kuslich et al. |
| 2010/0268231 A1 | 10/2010 | Kuslich |
| 2010/0286702 A1 | 11/2010 | Ahern et al. |

* cited by examiner

INTERSPINOUS MESH

CROSS-REFERENCE TO RELATED APPLICATION

This application is based on provisional patent application Ser. No. 60/958,149 filed Jul. 3, 2007.

BACKGROUND OF THE INVENTION

1. Field of the Invention

The present invention relates to methods and devices for the treatment of spinal stenosis.

2. Description of the Related Art

Spinal stenosis is a condition in which the spinal canal is narrowed, resulting in compression of the spinal cord and corresponding nerves. Possible causes of spinal stenosis include osteoarthritis, degenerative disc disease and other conditions associated with aging. Many people suffering from spinal stenosis often have spinous processes of adjacent vertebra that are abnormally close. Pressure on the spinal cord may be reduced by implanting a device that separates the spinous processes.

World Intellectual Property Organization (WIPO) Publication WO 2005/009300 describes a prosthesis inserted between spinous processes to prevent back pain. The prosthesis is comprised of an elastic material and includes a rigid central rod extended along its horizontal axis. The elastic material prevents leakage of liquids and gases and may be composed of rubber or silicon. Additionally, the prosthesis may have a dumbbell shape and may include expandable pockets within end sections and within a central section of the prosthesis. Prior to implantation, the pockets are filled with a substance, such as ethyl ether, that expands when exposed to body heat. The end sections are positioned along the sides of the spinous processes and the central section is positioned between the spinous processes.

WIPO Publication 2007/110604 discloses an expandable spacer including a flexible enclosure and a central tubular section extending along the horizontal axis of the enclosure. The flexible enclosure includes two end sections and a central section that may adapt to the shape of spinous processes when inserted between them. Further, the length of the central tubular section may be adjusted to stretch the flexible member so as to reduce the cross-sectional area of the spacer during insertion. After the spacer is inserted between spinous processes, the length of the central tubular section is reduced and the flexible enclosure is injected with a settable polymer resin through the central tubular section. Subsequent to polymerization, the end sections of the flexible enclosure retain the spacer in place and the pressure of the central section may control the separation between the spinous processes.

U.S. Pat. No. 5,549,679 discloses methods for treating spinal degeneration by inserting an expandable implant between vertebral bodies. The method may begin by boring out a portion of a degenerated disc and portions of neighboring vertebral bodies. Thereafter, the implant is inserted within the bored cavity and a bone graft material is injected within the implant. The implant is elliptical in shape and is porous, thereby enabling ingress and egress of fluids to permit growth of blood vessels, fibrous tissue and bone through the implant. The implant is sealed after it has been filled with the material. The patent also states that the filled implant may alternatively be positioned against the exterior lamina bone of adjacent vertebra to promote bone grafting of adjacent vertebra.

U.S. Pat. No. 7,226,481 and related U.S. Publication No. 2006/0149379 disclose methods for treating several spinal abnormalities including compression fractures by employing an implant similar to the patent described in U.S. Pat. No. 5,549,679. The references further describe inserting the implant within the vertebral body between vertebral end plates to displace diseased or damaged tissue or bone when filled with bone graft material.

SUMMARY OF THE INVENTION

It is an object of the invention to provide methods and implants for bone grafting the spinous processes to promote long term relief of back pain due to spinal stenosis.

It is further object of the present invention to provide minimally invasive surgical methods and implants for treating spinal stenosis by adjusting the position of adjacent vertebra.

These and other related objects are achieved according to the invention by a method for treating spinal stenosis including the steps of inserting a porous implant in interspinus space and filling the implant with a material to secure the implant and to adjust the position and orientation of adjacent vertebra. In accordance with one aspect of the present invention, the implant may be porous. According to another aspect of the present invention, the implant may include a central portion positioned between adjacent spinous processes and two end portions positioned along the sides of the implant to provide stability. Utilizing an implant with a central section and end sections in accordance with aspects of the present invention provide a significant advantage over the prior art. For example, as discussed above, prior art methods merely separate spinous processes with a foreign object. In contrast, the porosity of an exemplary implant of the present invention may permit bone grafting of adjacent spinous processes, thereby providing a durable and natural means for relieving spinal cord compression due to osteoarthritis and other causes of spinal stenosis, as discussed more fully below.

BRIEF DESCRIPTION OF THE DRAWINGS

The advantages, nature, and various additional features of the invention will appear more fully upon consideration of the illustrative embodiments now to be described in detail in connection with accompanying drawings. In the drawings.

DETAILED DESCRIPTION OF PREFERRED EMBODIMENTS

Figure 1A:
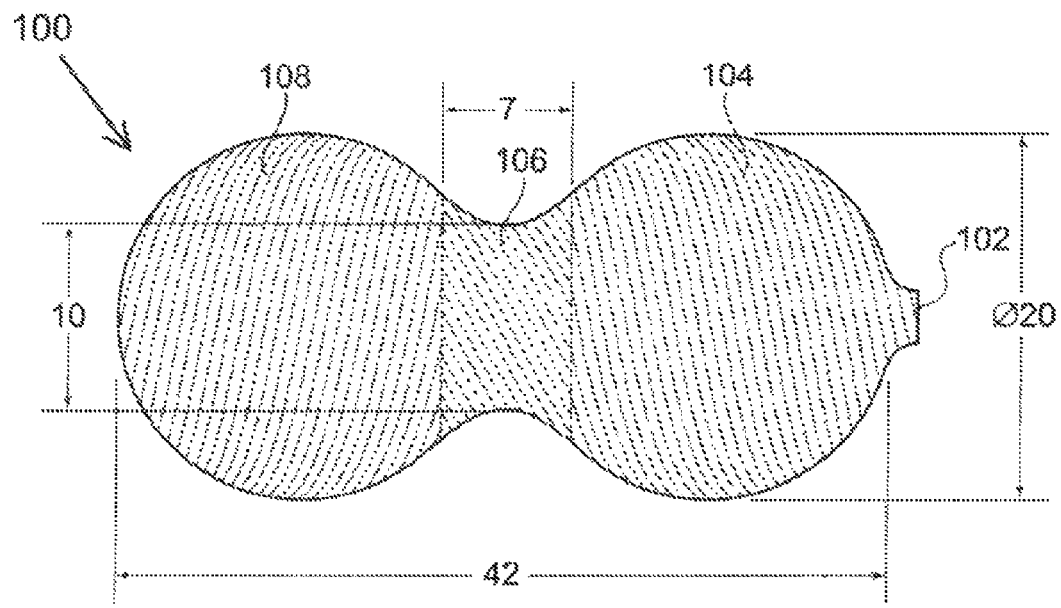
FIG. 1A is a diagram of an exemplary implant in a filled state in accordance with an aspect of the present invention.
Figure 1B:
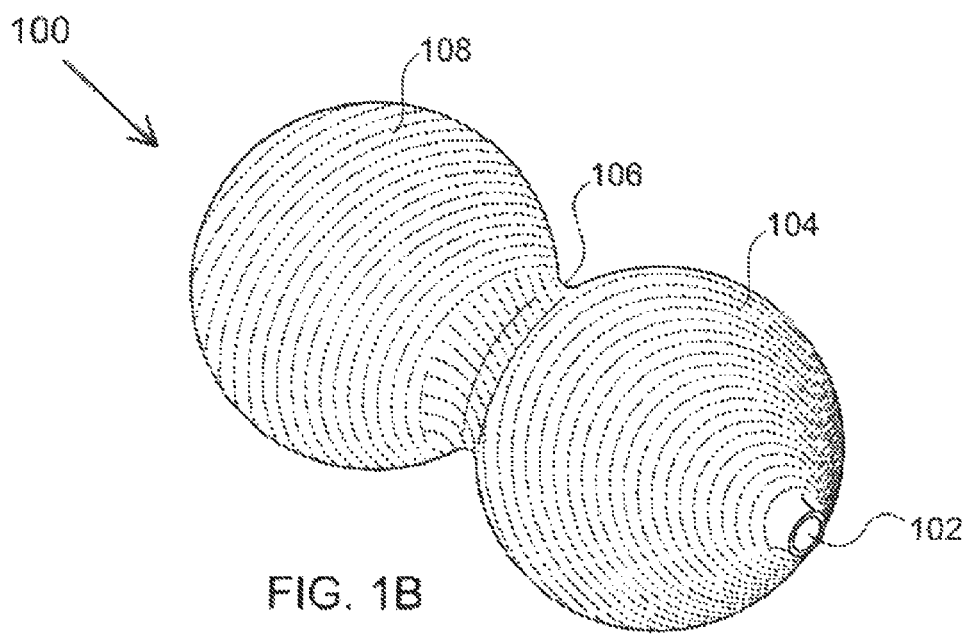
FIG. 1B is a diagram depicting an alternate view of an implant in a filled state in accordance with an aspect of the present invention.

The present invention provides methods and devices for treating spinal stenosis. According to one exemplary embodiment of the present invention, an implant may be inserted between the spinous processes of adjacent vertebra to adjust the position and orientation of the spinous processes, thereby relieving compression of the spinal cord. With reference to FIG. 1A and FIG. 1B, a view of an expanded implant 100 that is filled to a desired volume according to one aspect of the present invention is illustrated.

As depicted in FIGS. 1A and 1B, the implant 100 may be configured in a dumbbell or hour-glass shape, comprising four portions, described here from right to left: a fill insertion lip 102; a first end portion 104; a central portion 106; and a second end portion 108. The fill insertion lip 102 or fill opening may include an elliptical opening with a diameter sufficient to permit the insertion of a filling tube so that the implant 100 may be filled with a material to a desired volume. Moreover, the lip may be self-closing upon withdrawal of the tube or may be sealed as is known in the art. U.S. Pat. No. 5,549,679, for example, describes several known methods for sealing an implant.

Returning to FIGS. 1A and 1B, the first and second end portions 104 and 108 may be in a bulbous, elliptical configuration and may include corresponding elliptical cavities. The central portion may be in a catenoidal configuration and may include a corresponding catenoidal cavity, as shown in FIGS. 1A and 1B. According to one aspect of the present invention, the thinnest width 10 of the central portion cavity may be approximately half as large as the diameter 20 of one or both end portions. Further, the length 7 of the central portion may be approximately one-third the length 42 of the implant 100. However, it should be appreciated that the central portion and end portions need not be related as described above. For example, the width of the central portion may range from 2 mm and 15 mm, the length of the central portion may range from 2 mm to 17 mm, the widths of either end portion may be between 4 mm and 30 mm, and the length of the implant 100 may range from 8 mm to 56 mm.

Figure 2:
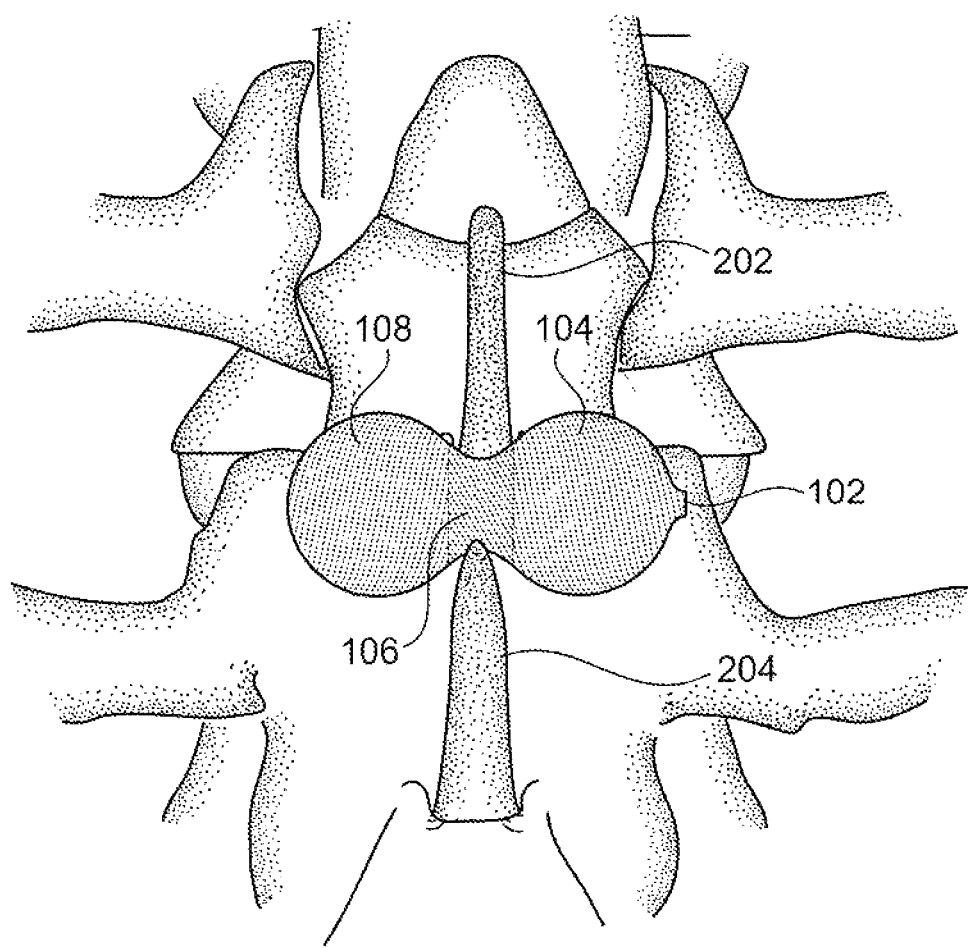
FIG. 2 is a diagram illustrating an exemplary implant in a filled state inserted between spinous processes in accordance with an aspect of the present invention.

With reference to FIG. 2, an illustration of a filled implant 100 inserted in an interspinous space is depicted. For example, as shown in FIG. 2, the central portion 106 of the filled implant 100 may be inserted between adjacent spinous processes 202 and 204 to adjust the position and orientation of the processes and the end portions 104 and 108 may be in contact with the sides of spinous processes 202 and 204 with sufficient surface pressure to secure the implant 100 in a proper location. Moreover, as shown in FIG. 2, the fill opening may permit access to a continuous space within said mesh bag. As discussed more fully below, the implant 100 may be porous to permit bone grafting of adjacent vertebra through the implant 100.

In accordance with a preferred embodiment the implant 100 is a porous, elastic, flexible and expandable bag that may exhibit strong tension characteristics when filled. For example, the implant 100 may be composed of any one or more of a polymeric fiber, fabric, metal and/or material used for surgical stitching. Further, it should be understood that the implant is composed of materials that are bio-compatible and meet all regulatory requirements. As depicted in FIGS. 1A and 1B, the implant may also include perforations in a mesh configuration. The perforations are of a sufficient size to prevent outflow of fill material while permitting the growth of blood vessels and bones through the implant in both the end portions and the central portion when filled with a bone graft particulate. For example, the pores may be sized between about 0.25 mm to about 5.0 mm. Bone grafting of adjacent spinous processes provides a significant advantage over merely separating spinous processes with a foreign object. For example, bone grafting of spinous processes enables the corresponding vertebrae to maintain a position and orientation for long-term relief of compression of a spinal cord due to a spinal stenosis condition.

Figure 3:
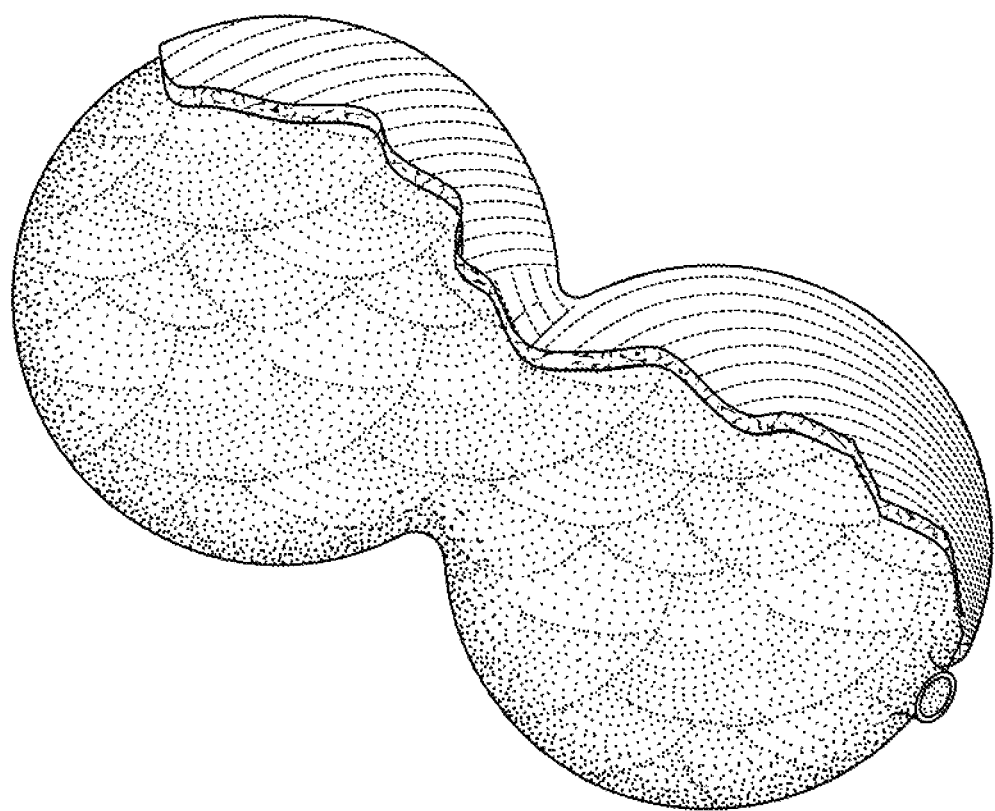
FIG. 3 is a diagram illustrating a cross-sectional view of an exemplary implant in a filled state in accordance with an aspect of the present invention.

With reference to FIG. 3, a cross-section of the filled implant showing the distribution of granular bone substitute utilized for bone grafting is illustrated. As depicted in FIG. 3, the implant perforations permit bone growth through the implant. In addition, the bone graft material inserted within the implant may comprise bone graft materials known in the art. For example, the bone graft material may include one or more of hydroxyapatite, morselized bone graft cortical, cancellous, bone morphogenic protein and calcified or decalcified bone derivative.

Figure 4:
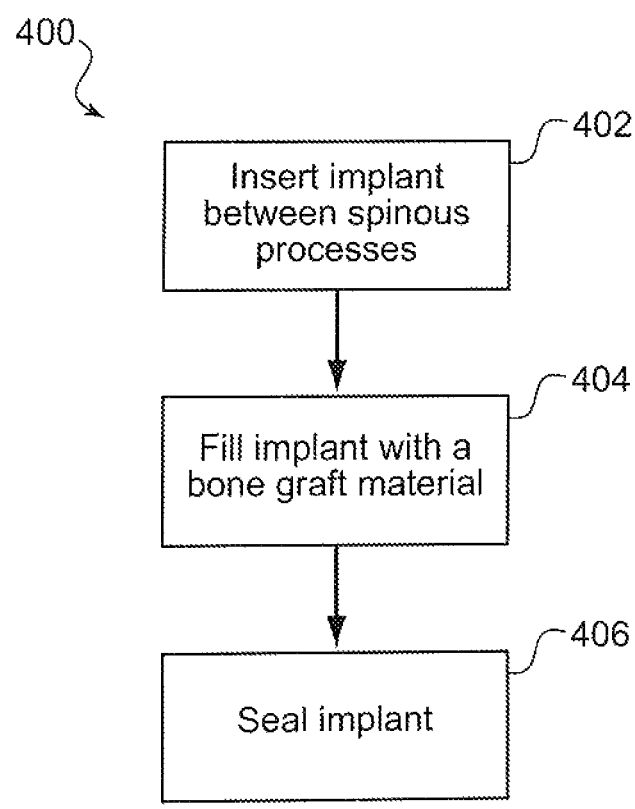
FIG. 4 is a high-level flow diagram illustrating an exemplary method for treating spinal stenosis in accordance with an aspect of the present invention.

Referring now to FIG. 4, a high-level method 400 for treating spinal stenosis is described. At step 402, the implant may be inserted in interspinous space in a variety of ways. For example, the implant may be inserted in interspinous space by inserting a guide tube percutaneously with an open end positioned between adjacent spinous processes. Subsequently, a fill tube having a diameter that is smaller than the diameter of the guide tube may be directed through the guide tube with the implant in a collapsed or empty state attached at the end of the fill tube. The implant may be attached to the fill tube by mating threads included along the inner surface of fill insertion lip 102 with threads included on the outer surface of the fill tube as is known in the art. Known attachment means and sealing means are described, for example, in U.S. Pat. No. 5,549,679.

After the implant is percutaneously pushed through the opening in the guide tube and situated in a proper position between the spinous processes, the implant may be filled with bone graft material in accordance with step 404, described more fully below. For example, the implant may be placed in a proper location and filled in to a desired volume and size by utilizing positioning methods know to those of ordinary skill in the art, such as, for example by including radiopaque materials within the implant and monitoring the implant in accordance with radiographic techniques.

It should also be noted that in other implementations, insertion of the guide tube may be omitted. For example, an incision may be made through a patient's soft tissue and the fill tube may be inserted through the incision with the implant tucked within the tube.

At step 404, with reference to FIG. 2, the implant may be filled with a bone graft material to a desired volume. For example, packing the implant with a material enables adjustment of the width of the central portion of the implant. The implant may be filled until the spinous processes are spaced a distance sufficient to relieve compression of the spinal cord due to spinal stenosis. Moreover, as the implant is filled over time, the bulbous end portions become increasingly rigid, thereby providing an increasing degree of stabilization along either side of the spinal processes. In this way the implant may adjust the position and orientation of the spinous processes. Further, the central portion of the implant may be positioned between adjacent spinous processes and the end portions may be positioned along the sides of the spinous processes to promote bone grafting as discussed above. In addition, the spinous processes with which the implant is in contact may be filed prior to filling the implant to enhance bone grafting, as is known in the art. FIG. 2 illustrates the implant inserted between spinous processes and filled to a desired volume.

At step 406, the implant may be sealed. For example, the fill insertion lip may be self sealing upon removal of the fill tube, as is known in the art.

Advantageously, method 400 may be performed percutaneously, thereby providing a minimally invasive procedure for implanting a spinal support device for the treatment of spinal stenosis.

Having described preferred embodiments for the treatment of spinal stenosis, materials used therein and methods for utilizing the same (which are intended to be illustrative and not limiting), it is noted that modifications and variations can be made by persons skilled in the art in light of the above teachings. It is therefore understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A spinal implant for use in adjusting the position and orientation of adjacent spinous processes comprising:
   a bone graft material; and
   a flexible and expandable biocompatible mesh bag containing bone graft material including
     two bulbous end portions of spherical shape configured to secure the implant in a position; and
     a central portion having a catenoidal shape and joining said end portions together having a width that is less than the widths of the at least two end portions that is configured to adjust the position and orientation of adjacent spinous processes by applying expansive pressure on the spinous processes when the catenoidal shaped portion of the biocompatible mesh bag is filled with the bone graft material.

2. The spinal implant of claim 1, wherein said mesh bag encloses a continuous space and said catenoidal shaped portion of said mesh bag surrounds a catenoidal shaped cavity which forms part of the continuos space within said mesh bag.

3. The spinal implant of claim 1, further comprising:
   a fill opening permitting access to a continuous space within said mesh bag.

4. The spinal implant of claim 3, wherein the fill opening is positioned along a central axis disposed in one of said end portions.

5. The spinal implant of claim 1, wherein the mesh of the central portion has pores with a porosity that permits bone grafting of the spinous processes through the implant.

6. The spinal implant of claim 5, wherein the pores are sized between about 0.25 mm to about 5.0 mm.

7. The spinal implant of claim 1, wherein the width of the central portion is between 2 mm and 15 mm and the widths of the end portions are between 4 mm and 30 mm.

8. The spinal implant of claim 1, wherein said mesh bag has an hour-glass shape when expanded.

* * * * *